(12) United States Patent
Suzuki

(10) Patent No.: US 10,610,182 B2
(45) Date of Patent: Apr. 7, 2020

(54) CONVERTING LOW-DOSE TO HIGHER DOSE 3D TOMOSYNTHESIS IMAGES THROUGH MACHINE-LEARNING PROCESSES

(71) Applicant: ALARA SYSTEMS, INC, Mountain View, CA (US)

(72) Inventor: Kenji Suzuki, Homewood, IL (US)

(*) Notice: Subject to any disclaimer, the term of this patent is extended or adjusted under 35 U.S.C. 154(b) by 244 days.

(21) Appl. No.: 15/360,276

(22) Filed: Nov. 23, 2016

(65) Prior Publication Data

US 2017/0071562 A1    Mar. 16, 2017

Related U.S. Application Data

(63) Continuation-in-part of application No. 14/596,869, filed on Jan. 14, 2015, now Pat. No. 9,730,660.
(Continued)

(51) Int. Cl.
*A61B 6/00* (2006.01)
*G06T 11/00* (2006.01)
(Continued)

(52) U.S. Cl.
CPC ............ *A61B 6/5205* (2013.01); *A61B 6/025* (2013.01); *A61B 6/502* (2013.01); *A61B 6/5211* (2013.01);
(Continued)

(58) Field of Classification Search
CPC ................. G03B 42/02; G06T 7/0012; G06T 2207/10081; G06T 2207/20016;
(Continued)

(56) References Cited

U.S. PATENT DOCUMENTS

2013/0051516 A1* 2/2013 Yang .................... A61B 6/03
378/4
2014/0153819 A1* 6/2014 Lin ...................... G06T 5/002
382/159

* cited by examiner

*Primary Examiner* — David E Smith
*Assistant Examiner* — Hsien C Tsai
(74) *Attorney, Agent, or Firm* — Cooper & Dunham LLP

(57) ABSTRACT

A method and system for converting low-dose tomosynthesis projection images or reconstructed slices images with noise into higher quality, less noise, higher-dose-like tomosynthesis reconstructed slices, using of a trainable nonlinear regression (TNR) model with a patch-input-pixel-output scheme called a pixel-based TNR (PTNR). An image patch is extracted from an input raw projection views (images) of a breast acquired at a reduced x-ray radiation dose (lower-dose), and pixel values in the patch are entered into the PTNR as input. The output of the PTNR is a single pixel that corresponds to a center pixel of the input image patch. The PTNR is trained with matched pairs of raw projection views (images together with corresponding desired x-ray radiation dose raw projection views (images) (higher-dose). Through the training, the PTNR learns to convert low-dose raw projection images to high-dose-like raw projection images. Once trained, the trained PTNR does not require the higher-dose raw projection images anymore. When a new reduced x-ray radiation dose (low dose) raw projection images is entered, the trained PTNR outputs a pixel value similar to its desired pixel value, in other words, it outputs high-dose-like raw projection images where noise and artifacts due to low radiation dose are substantially reduced, i.e., a higher image quality. Then, from the "high-dose-like" projection views (images), "high-dose-like" 3D tomosynthesis slices are reconstructed by using a tomosynthesis reconstruction algorithm. With the "virtual high-dose" tomosynthesis reconstruction slices, the detectability of lesions and clinically
(Continued)

important findings such as masses and microcalcifications can be improved.

28 Claims, 9 Drawing Sheets

Related U.S. Application Data

(60) Provisional application No. 61/927,745, filed on Jan. 15, 2014.

(51) Int. Cl.
*A61B 6/02* (2006.01)
*G06T 5/00* (2006.01)
*G06T 5/50* (2006.01)
*G06K 9/62* (2006.01)
*G06T 7/00* (2017.01)

(52) U.S. Cl.
CPC ............ *G06K 9/6262* (2013.01); *G06T 5/001* (2013.01); *G06T 5/50* (2013.01); *G06T 7/0014* (2013.01); *G06T 11/005* (2013.01); *A61B 6/461* (2013.01); *A61B 6/542* (2013.01); *G06T 2207/10116* (2013.01); *G06T 2207/20081* (2013.01); *G06T 2207/30068* (2013.01)

(58) Field of Classification Search
CPC . G06T 2207/20084; G06T 2207/20216; G06T 2207/30061; G06T 2207/30004; G06K 9/32; G06K 9/6256; A61B 6/484; A61B 6/4092; A61B 6/502
See application file for complete search history.

(a) Original 25% dose reconstructed slice (b) "Virtual" high-dose reconstructed slice for (a)

(c) Gold-standard real full-dose reconstructed slice (a) Input half-dose reconstructed slice  (b) "Virtual" high-dose reconstructed slice for (a)  (c) Gold-standard real full-dose reconstructed slice

CONVERTING LOW-DOSE TO HIGHER DOSE 3D TOMOSYNTHESIS IMAGES THROUGH MACHINE-LEARNING PROCESSES

REFERENCE TO RELATED APPLICATIONS

This patent application is a continuation-in-part, claims the benefit of, and hereby incorporates by reference parent U.S. patent application Ser. No. 14/596,869 filed Jan. 14, 2015 and published as US 2015-0196265 A1, which claims the benefit of U.S. Provisional Application No. 61/927,745 filed Jan. 15, 2014.

FIELD

This patent specification relates generally to the field of 3D breast imaging, also known as breast tomosynthesis, and more particularly to methods, systems, and computer programs for converting lower-dose tomosynthesis or other breast images into higher-dose-like tomosynthesis or other images.

This patent specification also generally relates to computerized techniques for automated analysis of digital images, for example, as discussed in one or more of U.S. Pat. Nos. 5,751,787; 6,158,888; 7,412,024; 8,378,302; 8,395,120; 6,819,790; 6,754,380; and 7,545,965, and U.S. Publication No. 2006/0018524, all of which are hereby incorporated by reference.

This patent specification can make use of technologies referenced and discussed in the above-noted U.S. Patents and Applications, as well as those discussed in the documents identified in the following List of References, which are cited throughout the specification by reference number (as providing supporting information) and are hereby incorporated by reference:

LIST OF REFERENCES CITED IN TEXT

[1] E. R. Myers, P. Moorman, J. M. Gierisch, L. J. Havrilesky, L. J. Grimm, S. Ghate, et al., "Benefits and Harms of Breast Cancer Screening: A Systematic Review," *JAMA*, vol. 314, pp. 1615-34, Oct. 20 2015.

[2] R. E. Bird, T. W. Wallace, and B. C. Yankaskas, "Analysis of cancers missed at screening mammography," *Radiology*, vol. 184, pp. 613-617, 1992.

[3] I. Andersson, D. M. Ikeda, S. Zackrisson, M. Ruschin, T. Svahn, P. Timberg, et al., "Breast tomosynthesis and digital mammography: a comparison of breast cancer visibility and BIRADS classification in a population of cancers with subtle mammographic findings," *Eur Radiol*, vol. 18, pp. 2817-25, December 2008.

[4] J. M. Park, E. A. Franken, Jr., M. Garg, L. L. Fajardo, and L. T. Niklason, "Breast tomosynthesis: present considerations and future applications," *Radiographics*, vol. 27 Suppl 1, pp. S231-40, October 2007.

[5] E. A. Rafferty, J. M. Park, L. E. Philpotts, S. P. Poplack, J. H. Sumkin, E. F. Halpern, et al., "Assessing Radiologist Performance Using Combined Digital Mammography and Breast Tomosynthesis Compared with Digital Mammography Alone: Results of a Multicenter, Multireader Trial," *Radiology*, vol. 266, pp. 104-113, 2013.

[6] M. A. Durand, B. M. Haas, X. Yao, J. L. Geisel, M. Raghu, R. J. Hooley, et al., "Early clinical experience with digital breast tomosynthesis for screening mammography," *Radiology*, vol. 274, pp. 85-92, January 2015.

[7] M. M. Bonafede, V. B. Kalra, J. D. Miller, and L. L. Fajardo, "Value analysis of digital breast tomosynthesis for breast cancer screening in a commercially-insured US population," *Clinicoecon Outcomes Res*, vol. 7, pp. 53-63, 2015.

[8] S. P. Zuckerman, E. F. Conant, B. M. Keller, A. D. Maidment, B. Barufaldi, S. P. Weinstein, et al., "Implementation of Synthesized Two-dimensional Mammography in a Population-based Digital Breast Tomosynthesis Screening Program," *Radiology*, p. 160366, Jul. 28 2016.

[9] S. A. Feig and R. E. Hendrick, "Radiation risk from screening mammography of women aged 40-49 years," *J Natl Cancer Inst Monogr*, pp. 119-24, 1997.

[10] M. J. Yaffe and J. G. Mainprize, "Risk of radiation-induced breast cancer from mammographic screening," *Radiology*, vol. 258, pp. 98-105, January 2011.

[11] S. Obenauer, K. P. Hermann, and E. Grabbe, "Dose reduction in full-field digital mammography: an anthropomorphic breast phantom study," *Br J Radiol*, vol. 76, pp. 478-82, July 2003.

[12] R. L. Smathers, J. M. Boone, L. J. Lee, E. A. Berns, R. A. Miller, and A. M. Wright, "Radiation dose reduction for augmentation mammography," *AJR Am J Roentgenol*, vol. 188, pp. 1414-21, May 2007.

[13] X. Liu, C. J. Lai, G. J. Whitman, W. R. Geiser, Y. Shen, Y. Yi, et al., "Effects of exposure equalization on image signal-to-noise ratios in digital mammography: a simulation study with an anthropomorphic breast phantom," *Med Phys*, vol. 38, pp. 6489-501, December 2011.

[14] M. Yakabe, S. Sakai, H. Yabuuchi, Y. Matsuo, T. Kamitani, T. Setoguchi, et al., "Effect of dose reduction on the ability of digital mammography to detect simulated microcalcifications," *J Digit Imaging*, vol. 23, pp. 520-6, October 2010.

[15] W. Huda, K. M. Ogden, E. M. Scalzetti, D. R. Dance, and E. A. Bertrand, "How do lesion size and random noise affect detection performance in digital mammography?," *Acad Radiol*, vol. 13, pp. 1355-66, November 2006.

[16] A. S. Chawla, E. Samei, R. Saunders, C. Abbey, and D. Delong, "Effect of dose reduction on the detection of mammographic lesions: a mathematical observer model analysis," *Med Phys*, vol. 34, pp. 3385-98, August 2007.

[17] G. Gennaro, L. Katz, H. Souchay, C. Alberelli, and C. di Maggio, "Are phantoms useful for predicting the potential of dose reduction in full-field digital mammography?," *Phys Med Biol*, vol. 50, pp. 1851-70, Apr. 21 2005.

[18] N. T. Ranger, J. Y. Lo, and E. Samei, "A technique optimization protocol and the potential for dose reduction in digital mammography," *Med Phys*, vol. 37, pp. 962-9, March 2010.

[19] E. Samei, R. S. Saunders, Jr., J. A. Baker, and D. M. Delong, "Digital mammography: effects of reduced radiation dose on diagnostic performance," *Radiology*, vol. 243, pp. 396-404, May 2007.

[20] K. C. Young, M. L. Ramsdale, and A. Rust, "Dose and image quality in mammography with an automatic beam quality system," *Br J Radiol*, vol. 69, pp. 555-62, June 1996.

[21] D. Gur, M. L. Zuley, M. I. Anello, G. Y. Rathfon, D. M. Chough, M. A. Ganott, et al., "Dose reduction in digital breast tomosynthesis (DBT) screening using synthetically reconstructed projection images: an observer performance study," *Acad Radiol*, vol. 19, pp. 166-71, February 2012.

[22] D. Bernardi, P. Macaskill, M. Pellegrini, M. Valentini, C. Fanto, L. Ostillio, et al., "Breast cancer screening with tomosynthesis (3D mammography) with acquired or synthetic 2D mammography compared with 2D mammography alone (STORM-2): a population-based prospective study," *Lancet Oncol*, vol. 17, pp. 1105-13, August 2016.

[23] M. J. Yaffe, "Reducing radiation doses for breast tomosynthesis?," *Lancet Oncol*, vol. 17, pp. 1027-9, August 2016.

[24] S. V. Destounis, P. DiNitto, W. Logan-Young, E. Bonaccio, M. L. Zuley, and K. M. Willison, "Can computer-aided detection with double reading of screening mammograms help decrease the false-negative rate? Initial experience," *Radiology*, vol. 232, pp. 578-84, August 2004.

[25] K. Suzuki, S. G. Armato, 3rd, F. Li, S. Sone, and K. Doi, "Massive training artificial neural network (MTANN) for reduction of false positives in computerized detection of lung nodules in low-dose computed tomography," *Med Phys*, vol. 30, pp. 1602-17, July 2003.

[26] K. Suzuki, I. Horiba, and N. Sugie, "Efficient approximation of neural filters for removing quantum noise from images," *IEEE Transactions on Signal Processing*, vol. 50, pp. 1787-1799, July 2002.

[27] K. Suzuki, I. Horiba, and N. Sugie, "Neural edge enhancer for supervised edge enhancement from noisy images," *IEEE Transactions on Pattern Analysis and Machine Intelligence*, vol. 25, pp. 1582-1596, December 2003.

[28] H. Arimura, S. Katsuragawa, K. Suzuki, F. Li, J. Shiraishi, S. Sone, et al., "Computerized scheme for automated detection of lung nodules in low-dose computed tomography images for lung cancer screening," *Academic Radiology*, vol. 11, pp. 617-629, June 2004.

[29] F. Li, H. Arimura, K. Suzuki, J. Shiraishi, Q. Li, H. Abe, et al., "Computer-aided detection of peripheral lung cancers missed at CT: ROC analyses without and with localization," *Radiology*, vol. 237, pp. 684-90, November 2005.

[30] K. Suzuki, J. Shiraishi, H. Abe, H. MacMahon, and K. Doi, "False-positive reduction in computer-aided diagnostic scheme for detecting nodules in chest radiographs by means of massive training artificial neural network," *Acad Radiol*, vol. 12, pp. 191-201, February 2005.

[31] K. Suzuki, H. Abe, F. Li, and K. Doi, "Suppression of the contrast of ribs in chest radiographs by means of massive training artificial neural network," in *Proc. SPIE Medical Imaging (SPIE MI)*, San Diego, Calif., 2004, pp. 1109-1119.

[32] K. Suzuki, H. Abe, H. MacMahon, and K. Doi, "Image-processing technique for suppressing ribs in chest radiographs by means of massive training artificial neural network (MTANN)," *IEEE Trans Med Imaging*, vol. 25, pp. 406-16, April 2006.

[33] S. Oda, K. Awai, K. Suzuki, Y. Yanaga, Y. Funama, H. MacMahon, et al., "Performance of radiologists in detection of small pulmonary nodules on chest radiographs: effect of rib suppression with a massive-training artificial neural network," *AJR Am J Roentgenol*, vol. 193, pp. W397-402, November 2009.

[34] K. Suzuki, F. Li, S. Sone, and K. Doi, "Computer-aided diagnostic scheme for distinction between benign and malignant nodules in thoracic low-dose CT by use of massive training artificial neural network," *IEEE Transactions on Medical Imaging*, vol. 24, pp. 1138-1150, September 2005.

[35] K. Suzuki, D. C. Rockey, and A. H. Dachman, "CT colonography: Advanced computer-aided detection scheme utilizing MTANNs for detection of "missed" polyps in a multicenter clinical trial," *Med Phys*, vol. 30, pp. 2-21, 2010.

[36] K. Suzuki, H. Yoshida, J. Nappi, S. G. Armato, 3rd, and A. H. Dachman, "Mixture of expert 3D massive-training ANNs for reduction of multiple types of false positives in CAD for detection of polyps in CT colonography," *Med Phys*, vol. 35, pp. 694-703, February 2008.

[37] K. Suzuki, H. Yoshida, J. Nappi, and A. H. Dachman, "Massive-training artificial neural network (MTANN) for reduction of false positives in computer-aided detection of polyps: Suppression of rectal tubes," *Med Phys*, vol. 33, pp. 3814-24, October 2006.

[38] J. Xu and K. Suzuki, "Massive-training support vector regression and Gaussian process for false-positive reduction in computer-aided detection of polyps in CT colonography," *Medical Physics*, vol. 38, pp. 1888-1902, 2011.

[39] K. Suzuki, J. Zhang, and J. Xu, "Massive-training artificial neural network coupled with Laplacian-eigenfunction-based dimensionality reduction for computer-aided detection of polyps in CT colonography," *IEEE Trans Med Imaging*, vol. 29, pp. 1907-17, November 2010.

[40] I. Sechopoulos, "A review of breast tomosynthesis. Part II. Image reconstruction, processing and analysis, and advanced applications," *Med Phys*, vol. 40, p. 014302, January 2013

[41] J. Zhou, B. Zhao, and W. Zhao, "A computer simulation platform for the optimization of a breast tomosynthesis system," *Med Phys*, vol. 34, pp. 1098-109, March 2007.

[42] T. Wu, A. Stewart, M. Stanton, T. McCauley, W. Phillips, D. B. Kopans, et al., "Tomographic mammography using a limited number of low-dose cone-beam projection images," *Med Phys*, vol. 30, pp. 365-80, March 2003.

[43] V. N. Vapnik, "Problem of Regression Estimation," in *Statistical Learning Theory*, ed New York: Wiley, 1998, pp. 26-28.

[44] S. Haykin, "Statistical Nature of Learning Process," in *Neural Networks*, ed Upper Saddle River, N.J.: Prentice Hall, 1998, pp. 84-87.

[45] V. N. Vapnik, "SV Machine for Regression Estimation," in *Statistical Learning Theory*, ed New York: Wiley, 1998, pp. 549-558.

[46] C. E. Rasmussen, "Gaussian processes for machine learning," 2006.

[47] V. N. Vapnik, "Least Squares Method for Regression Estimation Problem," in *Statistical Learning Theory*, ed New York: Wiley, 1998, p. 34.

[48] S. Haykin, "Back-Propagation Algorithm," in *Neural Networks*, ed Upper Saddle River, N.J.: Prentice Hall, 1998, pp. 161-175.

[49] J. Serra, *Image Analysis and Mathematical Morphology*. London: Academic Press, 1982.

[50] C. Dorai and A. Jain, "COSMOS—A representation scheme for 3D free-form objects," *IEEE Transactions on Pattern Analysis and Machine Intelligence*, vol. 19, pp. 1115-1130, October 1997.

[51] J. Koenderink and A. Vandoorn, "Surface shape and curvature scales," *Image and Vision Computing*, vol. 10, pp. 557-564, October 1992.

[52] Z. Wang, A. C. Bovik, H. R. Sheikh, and E. P. Simoncelli, "Image quality assessment: from error visibility to structural similarity," *IEEE Trans Image Process*, vol. 13, pp. 600-12, April 2004.

BACKGROUND

Mammography has been used in screening for breast cancer. The goal of screening mammography is the early detection of breast cancer through detection of masses and/or microcalcifications. Mammograms use doses of ionizing radiation usually at a lower-energy X-ray level (usually around 30 kVp).

The U.S. Preventive Services Task Force (USPSTF) recommended in 2009 screening of women aged between 50 and 74 with mammography every two years. The Canadian Task Force on Preventive Health Care and the European Cancer Observatory recommends mammography every 2-3 years between 50 and 69.

Three known challenges associated with mammography screening are: (1) false positive results (high recall rates), (2) false negative results, and (3) radiation exposure. False positives can lead to "overdiagnosis/overtreatment". A ten-year cumulative risk of a false-positive biopsy result in annual mammography screening is 7% [1]. A significant, if not the main, cause of false-negative results is high breast density that obscures breast tumors in 2D projection mammograms [2]. To improve breast imaging, including regarding false positives and negatives, digital breast tomosynthesis [3, 4] was developed. Breast tomosynthesis is a 3D imaging technology that takes multiple projections over a limited anguler range and reconstructs a 3D volume of slices (images of breast slices). An advantage of breast tomosynthesis over conventional 2D mammography is that breast tomosynthesis reduces the problem of tissue overlap present in a 2D projection mammogram and improves lesion conspicuity especially for dense breasts. Breast tomosynthesis has shown to be a promising modality for early detection of breast cancer, with higher cancer detection rates and fewer patient recalls (false positives) [3, 5-7].

With breast tomosynthesis, a remaining major challenge in breast cancer screening is radiation exposure. The FDA approved two scenarios with breast tomosynthesis: 1) breast tomosynthesis combined with conventional 2D mammography and 2) breast tomosynthesis with synthesized 2D "mammograms" obtained from a 3D breast tomosynthesis volume. In the two scenarios, the radiation dose (5-8 mGy) [8] to the radiosensitive breasts in breast tomosynthesis can be 1.4-2.3 times higher than the conventional 2D digital mammography radiation dose (about 3.5 mGy). Repeated breast tomosynthesis for annual screening could increase cumulative radiation exposure and lifetime attributable risks for radiation-induced breast cancer. A recent study conducted by Drs. Martin Yaffe and James Mainprize estimated that 11 deaths from 86 radiation-induced breast cancers would occur within a cohort of 100,000 women each receiving a dose of 3.7 mSv during annual mammographic screening. Based on the study results [9, 10] for mammography screening, annual breast tomosynthesis screening of women starting at age 40 years could cause one life lost due to radiation-induced cancer per 18.9-47.4 lives saved. Therefore, radiation dose reduction is important for breast cancer screening with breast tomosynthesis. This patent specification discloses an innovative radiation dose reduction technology designed to help with the challenge of radiation dose in breast tomosynthesis.

When a radiologist or a computer detects, interprets, analyzes, and diagnoses breast images, there is a tradeoff between radiation dose levels and image quality. Higher radiation doses generally result in higher signal-to-noise ratio, while lower doses generally lead to increased image noise including quantum noise and electronic noise. Higher radiation exposure and dose would increase the risk of radiation-induced cancer. Therefore, it is important to reduce radiation exposures and dose as much as practicable and reasonably achievable.

Researchers have studied radiation dose reduction in mammography. S. Obenauer et al. [11] compared full-field digital mammography with screen-film mammography, and investigated a potential of dose reduction with an anthropomorphic breast phantom by changing anode-filter combinations in full-field digital mammography. R. L. Smathers et al. [12] evaluated the effects of anode-filter combinations on radiation dose reduction in mammography with 206 clinical cases. They showed that changing anode-filter combinations could reduce radiation dose by 35%. X. Liu et al. [13] investigated the effects of exposure equalization on the image quality and radiation dose reduction with an anthropomorphic breast phantom. They showed that the exposure equalization technique could reduce radiation dose by 34%. M. Yakabe et al. [14] investigated the relationship between radiation dose and the detectability of simulated microcalcifications with an anthropomorphic breast phantom. The radiation dose was changed by changing tube-current-time-product, mAs. W. Huda et al. [15] investigated the effects of random noise and lesion size on the detection performance by radiologists with an anthropomorphic breast phantom. A. S. Chawla et al. [16] investigated the effect of radiation dose reduction on the detection of breast lesions with simulated noise by using mathematical observer model analysis. G. Gennaro et al. [17] evaluated the phantom use in radiation dose reduction in mammography. N. T. Ranger et al. [18] investigated optimization of tube voltage, kVp and anode-filter combinations in mammography. E. Samei et al. [19] assessed the relationship between radiation dose and observer accuracy in the detection of simulated lesions in mammography. K. C. Young et al. [20] assessed the automatic beam quality selection function of a vendor's mammography system.

To help with the radiation dose issue in breast tomosynthesis, researchers have developed a technique to create a 2D image synthesized from 3D images, which can eliminate a necessity of separate acquisition of a 2D mammogram [21, 22]. Yaffe [23] pointed out, however, that even with use of the 2D synthetic image, radiation dose from 3D breast tomosynthesis can still be an issue, because radiation dose of 3D breast tomosynthesis can be higher than that of 2D mammography. In fact, the radiation dose by breast tomosynthesis with a 2D synthetic "mammogram" (5 mGy) [8] can still be 1.4 times higher than a typical mammography radiation dose. In addition, because the synthetically created 2D images may appear different from real 2D mammograms that radiologists have been accustomed to, acceptance of the synthetic images by radiologists may still be an issue. Therefore, it is important to reduce radiation dose of breast tomosynthesis, at least to the level of the mammography radiation dose. If radiation dose is simply reduced, more noise and artifact appear in breast tomosynthesis slices, which may obscure subtle lesions and patterns such as microcalcifications. A noise reduction filter may be used, but it tends to smooth out subtle patterns and tiny microcalcifications together with noise. In addition, it may not reduce artifact. Thus, it is a challenge to reduce noise and artifact in breast tomosynthesis slices while maintaining diagnostic information and depiction of subtle lesions. (The terms slice and slice image are used interchangeably in this patent specification, as is often done in breast tomosynthesis technology, although strictly speaking a breast slice is a physical object and a slice image is an image of that physical object.)

Computer-aided diagnostic (CAD) systems are being tested to decrease the number of cases of cancer that are missed in mammograms. In one test, a computer identified 71% of the cases of cancer that had been missed by physicians. However, the computer also flagged twice as many non-cancerous masses than the physicians did. In a second study of a larger set of mammograms, a computer recommended six biopsies that physicians did not. All six turned out to be cancers that would have been missed [24].

In the field of CAD, K. Suzuki et al. developed a pixel-based machine-learning technique based on an artificial neural network (ANN), called massive-training ANNs (MTANN), for distinguishing a specific opacity (pattern) from other opacities (patterns) in 2D CT images [25]. An MTANN was developed by extension of neural filters [26] and a neural edge enhancer [27] to accommodate various pattern-recognition and classification tasks [25]. The 2D MTANN was applied to reduction of false positives (FPs) in computerized detection of lung nodules on 2D CT slices in a slice-by-slice way [25, 28, 29] and in chest radiographs [30], the separation of ribs from soft tissue in chest radiographs [31-33], and the distinction between benign and malignant lung nodules on 2D CT slices [34]. For processing of three-dimensional (3D) volume data, a 3D MTANN was developed by extending the structure of the 2D MTANN, and it was applied to 3D CT colonography data [35-39].

SUMMARY OF THE DISCLOSURE

This patent specification describes converting lower-quality, lower-dose 3D breast images (or lower-quality, lower-dose 3D tomosynthesis slices or other 3D images) with noise into higher quality, less noise, less artifact, higher-dose-like 3D breast images (or higher-dose-like 3D tomosynthesis slices). The described method and system use a trainable nonlinear regression (TNR) model with a patch-input-pixel-output scheme, which can be called pixel-based TNR (PTNR). A 3D tomosynthesis system acquires multiple projection views (images) of a breast over a limited angle range to reconstruct a 3D volume of high-resolution slices or other 3D images of the breast such as a 3D volume image. In a preferred example, an image patch is extracted from multiple input 2D raw projection views (as a form of images) of a breast acquired at a reduced x-ray radiation dose (lower-dose), and pixel values in the patch are entered into the PTNR as input. The output of the PTNR is a smaller patch, preferably a single pixel, that can correspond to the center pixel of the input image patch. The PTNR receives such patches, for example a respective patch for each pixel of the input image in a raster or some other pattern. The PTNR is trained with matched pairs of raw projection views (images), inputting lower-dose raw projection views (images) together with corresponding desired higher x-ray radiation dose raw projection views (images) (higher-dose views or images), such as standard dose tomosynthesis views or higher-than-standard-dose tomosynthesis views, which are ideal images for the output images. The desired higher-dose x-ray 2D raw projection views may be acquired at up to the highest (or approximately the highest) radiation dose level that the tomosynthesis system can generate or use for practical purposes.

Through the training, the PTNR learns to convert lower-dose 2D raw projection views (images) to high-dose-like 2D raw projection views (images). Once trained, the trained PTNR does not require the higher-dose tomosynthesis acquisitions anymore. When a new reduced x-ray radiation dose (low dose) 2D raw projection view (image) is entered, the trained PTNR would output a pixel value similar to the corresponding desired pixel value, in other words, it would output high-dose-like 2D raw projection views (images) where noise and artifacts due to low radiation dose are substantially reduced, i.e., views or images with a higher image quality. Note that the new low-dose 2D raw projection views do not have to be acquired at a lower radiation dose level than a standard dose, but they can be acquired at any radiation-dose level lower than the highest radiation dose that the tomosynthesis system can generate or use for practical purposes. Then, from the "high-dose-like" projection views (images), "high-dose-like" 3D tomosynthesis slices (slice images) are reconstructed by using a tomosynthesis reconstruction algorithm [40] such as filtered back-projection [41] and an iterative reconstruction method [42]. The "high-dose-like" 3D tomosynthesis slices where noise and artifact are substantially reduced can be expected to be similar to real high-dose 3D tomosynthesis slices; thus they may be called "virtual" high-dose 3D tomosynthesis slices. With the "virtual high-dose" 3D tomosynthesis slices, the detectability of lesions and clinically important findings such as masses and microcalcifications can be improved. The reconstruction can produce virtual hi-dose other 3D views such as a 3D volume of voxel values for the entire breast or a volume region of interest in the breast, for example by stacking virtual high-dose slices or portions of slices. This patent specification further describes a computer program product that stores in computer-readable media, in non-transitory form, instructions that when loaded into and executed by a computer system carry out the processes described herein.

DETAILED DESCRIPTION

In preferred examples, the systems and methods described in this patent specification use a pixel-based trainable non-linear regression (PTNR) that converts lower-dose raw projection views (as a form of images) of a breast to higher-quality, higher-dose-like raw projection views (images) of the breast. Lower-dose raw projection views (images) are of lower image quality, with more noise, than the higher-quality, higher-dose-like raw projection views (images). Higher-dose-like raw projection views (images) look like real, high-dose raw projection views (images) that are of higher image quality with less noise or artifacts than the lower-dose raw projection views (images). The PTNR system uses a trainable nonlinear regression (TNR) model that processes pixels in patches (or regions) in raw projection views (images). There are two main steps associated with PTNR: (1) a design step to determine the parameters in PTNR by using designing pairs of lower-dose (lower image quality) and higher-dose (higher image quality) raw projection images and (2) a conversion step to convert low-dose raw projection views (images) to higher-dose-like raw projection views (images) or "virtual high-dose" raw projection views (images) where noise and artifacts are eliminated or at least substantially reduced. A reconstruction process follows to form 3D breast images from the virtual high-dose raw projection views (images).

Figure 1A:
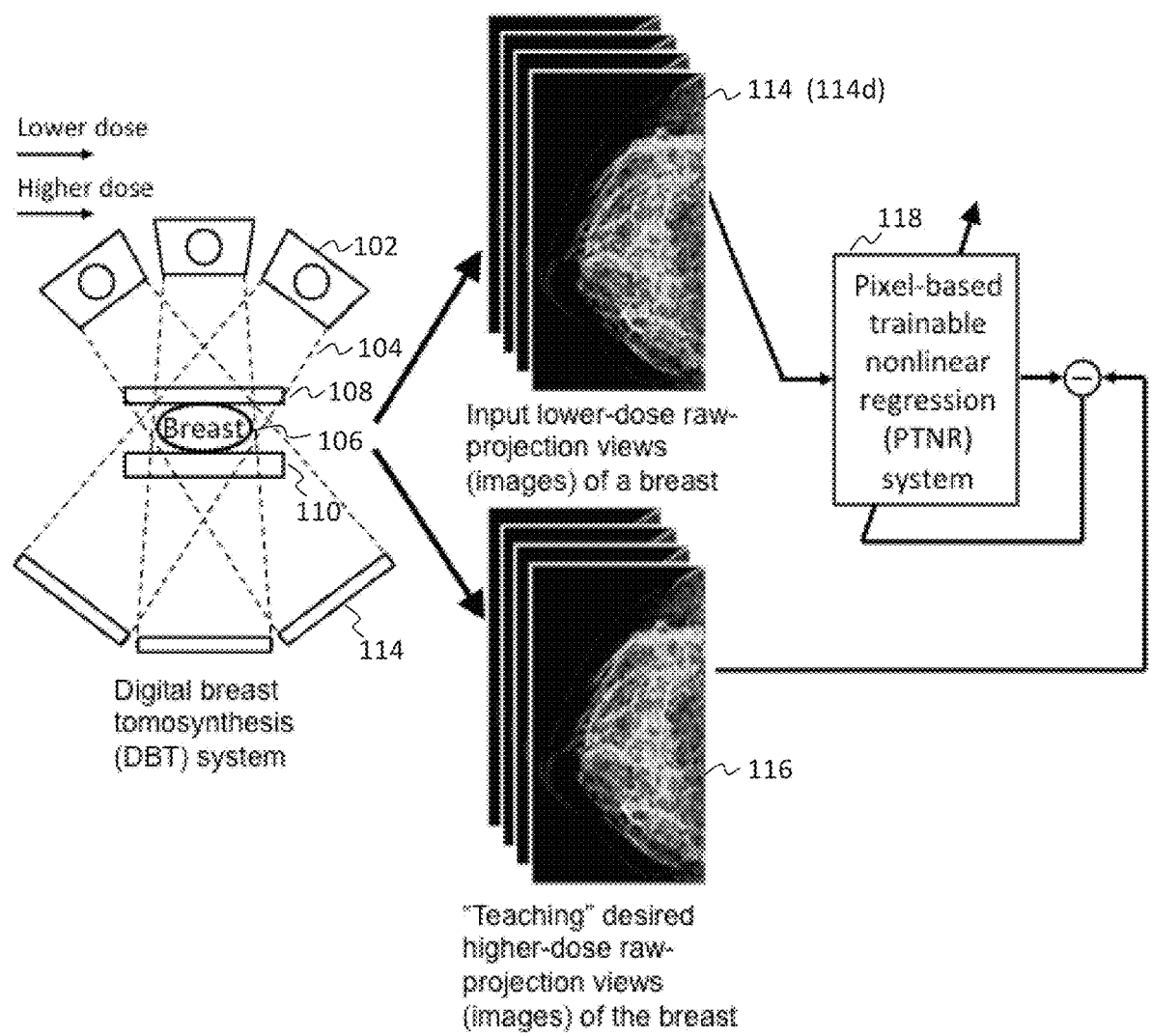
FIG. 1A shows a schematic diagram of a PTNR system for projection views or images in a design step.

FIG. 1A shows a schematic diagram of a PTNR system and method in a design step. In the design step, the PTNR system 118 is designed with input lower-dose 2D raw projection views (images) 114 with more noise and the corresponding desired higher-dose 2D raw projection views (images) 116 with less noise or artifact. For example, as illustrated in FIG. 1A, a breast imaging structure comprises an x-ray source 102 shown in three angular positions from which is emits an imaging x-ray beam 104 that passes through a breast 106 compressed between a compression paddle 108 and a breast platform 110. A 2D image receptor 112, shown in three positions corresponding to the positions of x-ray source 102, produces tomosynthesis 2D raw projection views or images. The structure can operate in a low-mAs mode to produce low-dose, lower image quality 2D raw projection views (images), or in a high-mAs mode to produce higher-dose, higher image quality 2D raw projection views (images), such as 2D raw projection views (images) taken at the dose recommended by the current Mammogram Quality Standards Act (MQSA) for standard screening mammograms (e.g., 3.7-4.2 mGy average mean glandular radiation dose for 2-view mammograms of a patient's breasts) or at higher dose. The higher-dose raw projection views (images) may be acquired at up to the highest (or approximately the highest) radiation dose level that the tomosynthesis system can generate or use for practical purposes. The parameters in the PTNR system and method are adjusted to minimizing the difference between the input images and the corresponding desired 2D raw projection views (images). Through the designing process, the PTNR system learns to convert lower-dose 2D raw projection views (images) being lower-image-quality with more noise to higher-dose-like 2D raw projection views (images) being higher-image-quality with less noise or artifact.

Figure 1B:
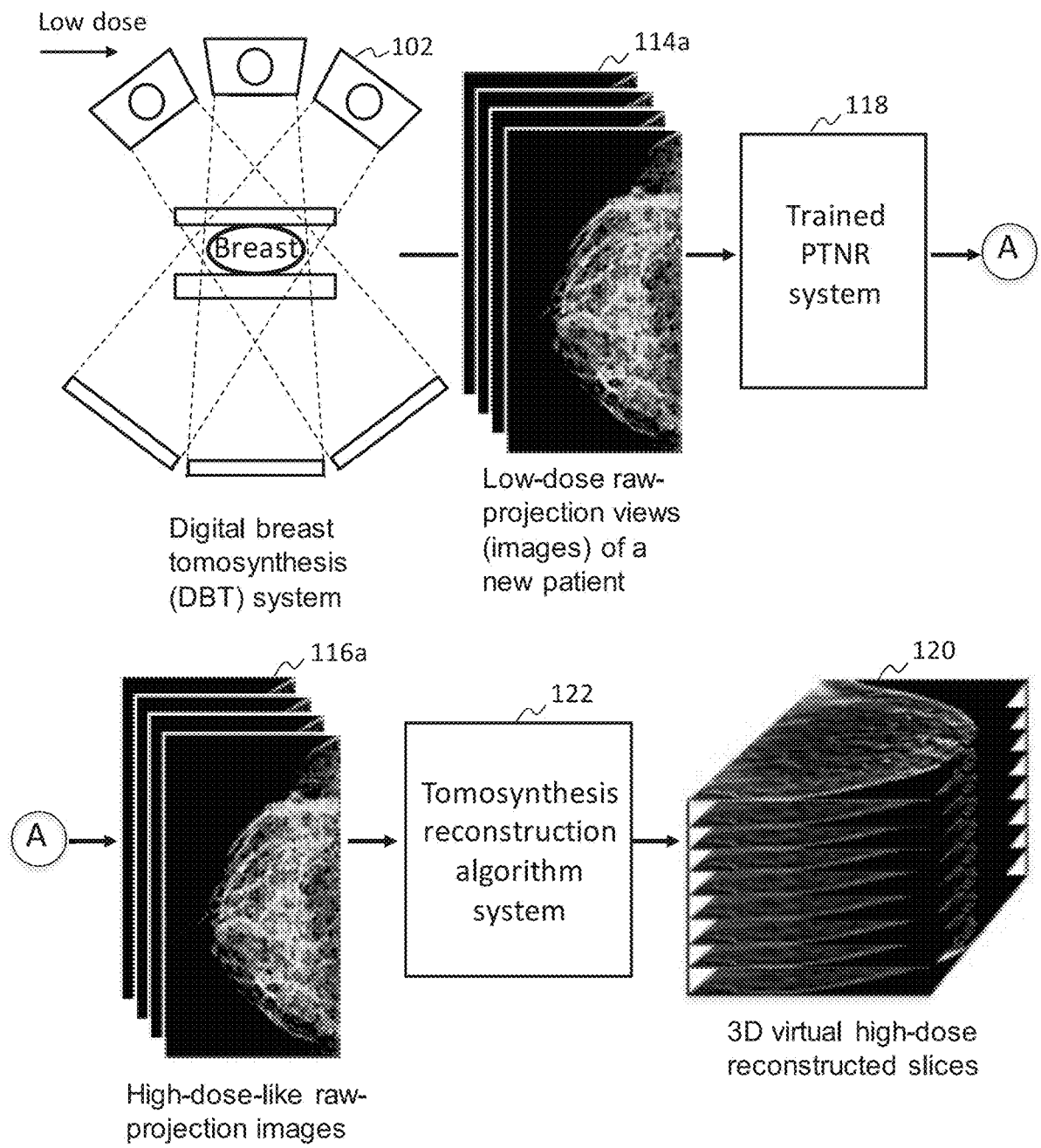
FIG. 1B shows a schematic diagram of a PTNR system for projection vies or images in a conversion step.

FIG. 1B shows a schematic diagram of a PTNR system and method in a conversion step. Once the PTNR system is trained, the trained PTNR does not require higher-dose 2D raw projection views (images) anymore. When new reduced radiation dose (low dose) raw projection views (images) are obtained by operating x-ray source 102 of the breast imaging structure in its lower dose mode and are entered, the trained PTNR system 118 would output images 116a similar to their corresponding desired images, in other words, it would output high-dose-like high-quality 2D raw projection views (images) or "virtual high-dose" 2D raw projection views (images) 116a where noise and artifacts due to lower radiation dose are substantially reduced. Note that the new low-dose 2D raw projection views 114a do not have to be acquired at a lower radiation dose level than a standard dose (such as the one recommended by the current MQSA for screening mammograms or diagnostic mammograms), but they can be acquired at any radiation-dose level lower than the highest radiation dose that the tomosynthesis system can generate or use for practical purposes. The noise in low-dose 2D raw projection views (images) 114a contains two different types of noise: quantum noise and electronic noise. Quantum noise is modeled as signal-dependent noise, and electronic noise is modeled as signal-independent noise. The PTNR system 118 is expected to eliminate or at least substantially reduce both quantum noise and electronic noise. In addition to noise characteristics, the conspicuity of breast tissue such as masses (or tumors), architectural distortion (early sign of breast cancer), milk ducts, breast cancer including ductal carcinoma in situ, and microcalcifications in higher-dose 2D raw projection views (images) 116a is higher than that of such objects in lower-dose 2D raw projection views (images) 114a. From the "high-dose-like" raw projection images 116a provided by the designed PTNR system 118, "high-dose-like" 3D tomosynthesis slices 120 are reconstructed by using a tomosynthesis reconstruction algorithm [40] system 122 applying to images 116a processes such as filtered backprojection [41] and an iterative reconstruction [42]. The "high-dose-like" 3D tomosynthesis slices 120 where noise and artifact are substantially reduced are expected to be similar to real high-dose 3D tomosynthesis slices; thus they may be called "virtual" high-dose 3D tomosynthesis slices 120. Therefore, the PTNR system 118 combined with the tomosynthesis reconstruction algorithm system 122 is expected to improve the conspicuity of normal and abnormal structures in 3D tomosynthesis slices 120. With improved 3D tomosynthesis slices 120, radiologists' diagnostic performance, namely, regarding sensitivity and specificity of lesions would be improved; and thus, parameters regarding mortality and incidence of breast cancer as well as other breast diseases would potentially be improved with the PTNR-converted tomosynthesis slices 120 or other 3D views based on slices 120.

The PTNR system 118 can use a trainable nonlinear regression (TNR) model, the formulation of which is described in [43], with a patch-input-pixel-output scheme. See, for example pages 26-28 in [43]. The TNR may be a regression model such as an artificial neural network regression model, the formulation of which is descried in [44]), (see, for example pages 84-87 in [44]), a support vector regression model, the formulation and theory of which is descried in [45] (see, for example pages 549-558 in [45]), shallow or deep convolutional neural networks, shift-invariant neural networks, deep learning, deep belief networks, similarity learning, sparse dictionary learning, manifold learning, dictionary learning, Kernel machines, random forest regression, a bag of visual words, and a nonlinear Gaussian process regression model, the formulation and theory of which is descried in [46]. Other regression models or machine-learning models may be used such as a nearest neighbor algorithm, association rule learning, inductive logic programming, reinforcement learning, representation learning, similarity learning, sparse dictionary learning, manifold learning, dictionary learning, boosting, Bayesian networks, case-based reasoning, Kernel machines, subspace learning, Naive Bayes classifiers, ensemble learning, random forest, decision trees, and statistical relational learning. Among the above models, classifier models such as Naive Bayes classifiers, Bayesian networks, random forest, and decision trees can be used in the PTNR system 118, but the performance of the PTNR system 118 may not be as high as the use of a regression model. In a preferred process used in PTNR system 118, first an image patch is extracted from an input view or image that is acquired at a reduced x-ray radiation dose (lower dose). Pixel values in the image patch are entered into the PTNR system 118 as input. The output of the PTNR system 118 in this example preferably is a single pixel O(x,y,z) that corresponds to the center pixel in the input image patch, represented by $$O(x,y,z)=\text{TNR}\{I(x,y,z)\}, \quad (1)$$

$$I(x,y,z)=\{g(x-i,y-j,z-k)|(i,j,k)\in P\}, \quad (2)$$

where TNR is a trainable regression model, I(x,y,z) is the input vector, x, y, and z are the image coordinates, g(x,y,z) is an input raw projection view (image), P is an image patch, and i, j, and k are variables. z is the image coordinate associated with the angle of the x-ray-source to detector path when multiple projection views are acquired with a tomosynthesis system. When the TNR is applied to 3D tomosynthesis reconstructed slices, as in the example of FIGS. 3a and 3b, z is the image coordinate associated with the axis along the slice number.

Figure 3A:
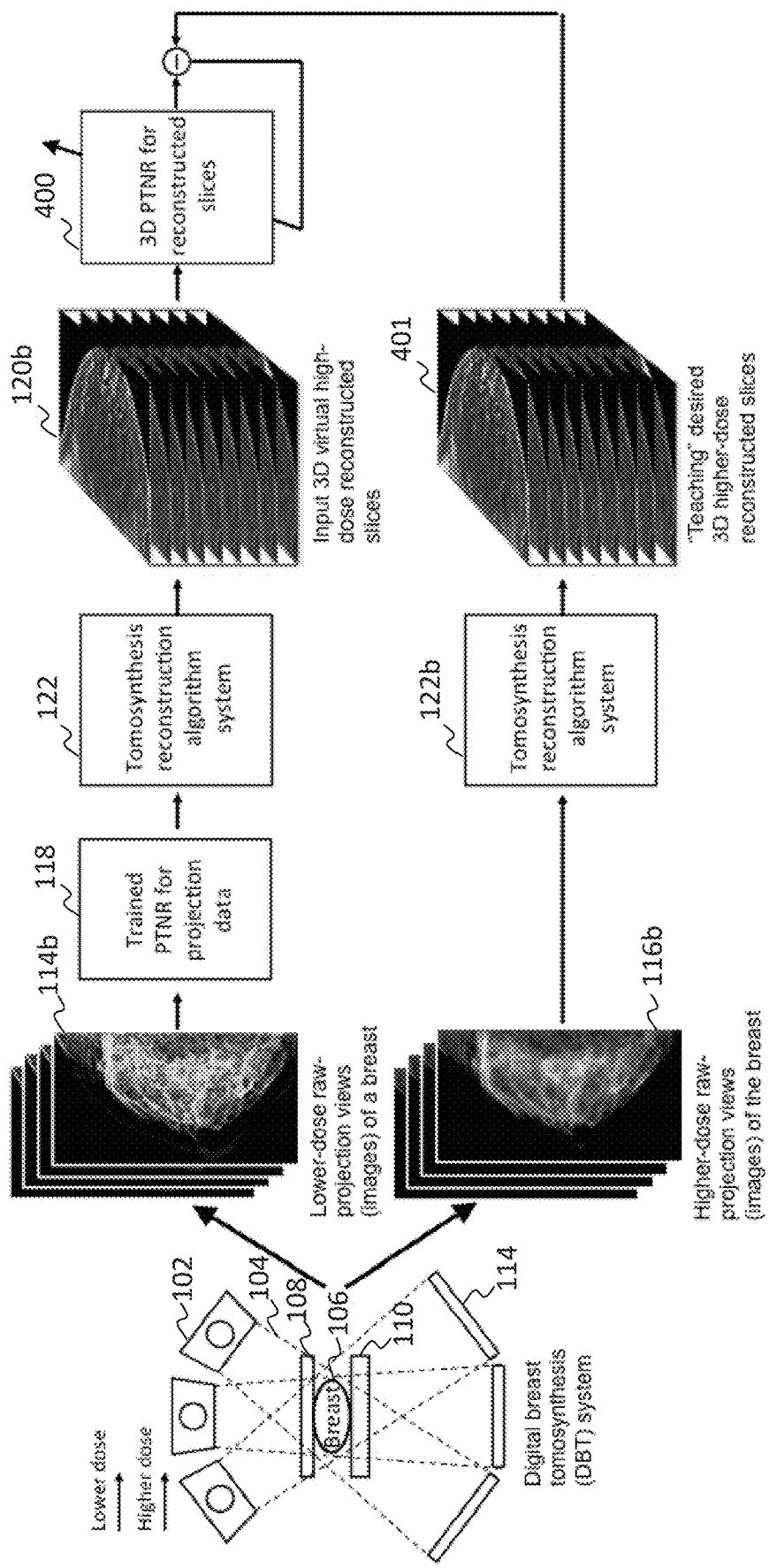
FIG. 3A shows a schematic diagram of a PTNR system for reconstructed slices or slice images in a design step.
Figure 3B:
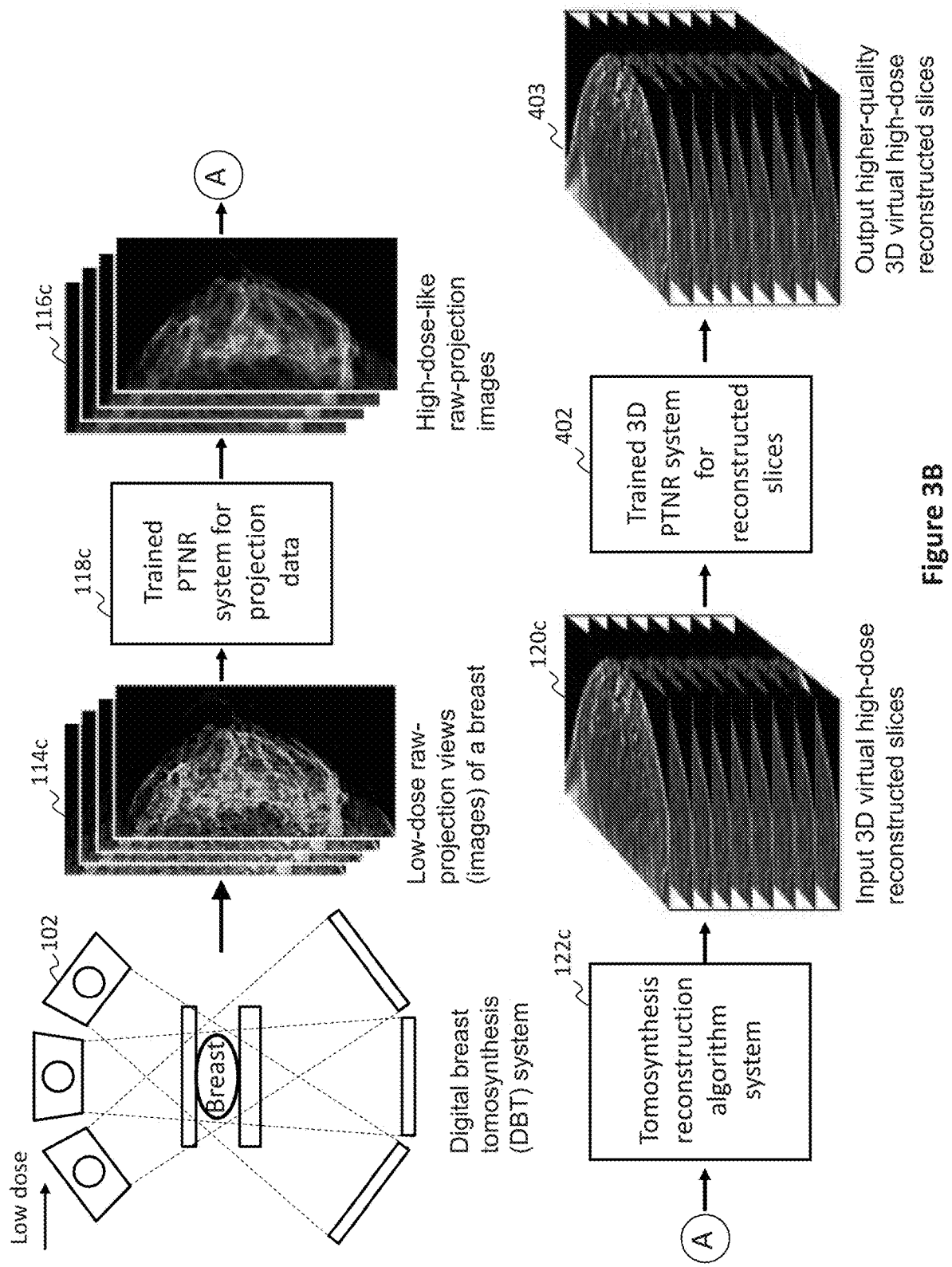
FIG. 3B shows a schematic diagram of a PTNR system for reconstructed slices or slice images in a conversion step.

To locate the center of the image patch accurately, the size of the image patch is preferably an odd number. In the case of processing 2D projection images such as images or views 114 and 114a, a patch is a grouping of pixels or pixel values, such as a 3×3, 5×5, or larger group of pixels of their values, but can be an even-numbered groups. In the more general case, and in the case of processing 3D slices or slice images as discussed below in connection with FIGS. 3a and 3b below, a patch can be a 3D grouping of voxels or voxel values, and the size of the image patch may be 3×3×3, 5×5×5, 7×7×7, 9×9×9, 11×11×11, 13×13×13, 15×15×15 pixels or larger. However, the size of the image patch can be an even number, such as 2×2×2, 4×4×4, and 5×5×5 pixels. The image patch when two-dimensional preferably is a square or rectangle but can be other shapes such as a circle, an oval, or an irregular shape. When 3D, the image patch can be a cube of square but other array shapes can be used, such as sphere, circle, rectangular or rounded or even irregular. To obtain an entire output image, each pixel in the output image is derived by converting a patch of the input image by using the PTNR system 118. Converted pixels outputted from the TNR system 118 are arranged and put into the corresponding pixel positions in the output image, which forms an output "virtual high-dose" raw projection images. In the example of FIGS. 3a and 3b, the output values can be the pixel values of a slice image.

In the design step of FIG. 1a, first, a large number of image patches together with the corresponding desired pixel values are acquired from the input lower-dose 2D raw projection views (images) 114 and desired higher-dose 2D raw projection views (images) 116, respectively. Input vectors are calculated from the image patches. The input vectors are then entered to the PTNR model of system 118 as input. Output pixel values from the PTNR system 118 are calculated based on the current parameters in the model. Then, the output pixel values are compared with the corresponding desired pixel values in the desired 2D raw projection views (images) 116, and the difference "d" between the two is calculated, for example, represented by $$d = \sum_{p} \{D^{(p)} - O^{(p)}\}^2, \quad (3)$$

where D is the p-th pixel value in the desired output image 116, and O is the p-th pixel value in the output raw projection images from system 118.

The parameters in the TNR model are adjusted so as to minimize or at least reduce the difference. A method to minimize the difference between the output and the desired value under the least square criterion [47], that uses mean square errors between output pixel values and their desired pixel values, may be used to adjust the TNR model. See, for example page 34 in [47]. Other minimizing criterion (or cost function) can be used, such as the least mean absolute error criterion, and the least root mean square error criterion. The difference calculation and the adjustment are repeated. As the adjustment proceeds, the output pixel values and thus the output 2D raw projection images become closer to the corresponding desired higher-dose 2D raw projection images. When a stopping condition is fulfilled, the adjustment process is stopped. The stopping condition may be set as, for example, (a) an average difference is smaller than a predetermined difference, or (b) the number of adjustments is greater than a predetermined number of adjustments. After training, the PTNR system 118 would output "virtual high-dose" 2D raw projection views (images) that are the same or nearly the same as views (images) 116 where noise and artifacts due to low radiation dose are substantially reduced. With the higher-quality "virtual high-dose" 2D raw projection images matching images 116 or their use to reconstruct 3D images, the detectability of lesions and clinically important findings such as masses and microcalcifications can be improved.

In a modified PTNR system 118, an extractor for morphologic elements including "impulsive" small high brightness regions is added to the basic PTNR process. Low-dose 2D raw projection images 114 are entered to the extractor to obtain images that extract or enhance morphologic elements including "impulsive" small high brightness regions. The "impulsive" small high brightness regions may be microcalcifications. Thus, one kind of the output images of the extractor may be considered as microcalcification-extracted images. Image patches are extracted from both original low-dose 2D raw projection images 114 and morphologic-elements-extracted images, where the image patches extracted from the original low-dose 2D raw projection images may be larger or equal to those extracted from morphologic-elements-extracted images. The size of the image patches extracted from the morphologic-elements-extracted images may be as small as one single pixel. The extracted image patches form an input vector to the TNR system 118.

In the design step, image patches extracted from both original low-dose 2D raw projection images 114 and morphologic-elements-extracted images form an input vector to the TNR. Output pixels are calculated based on the input vector, and parameters are adjusted to minimize the difference between the output pixels and the corresponding teaching pixels.

Figure 2A:
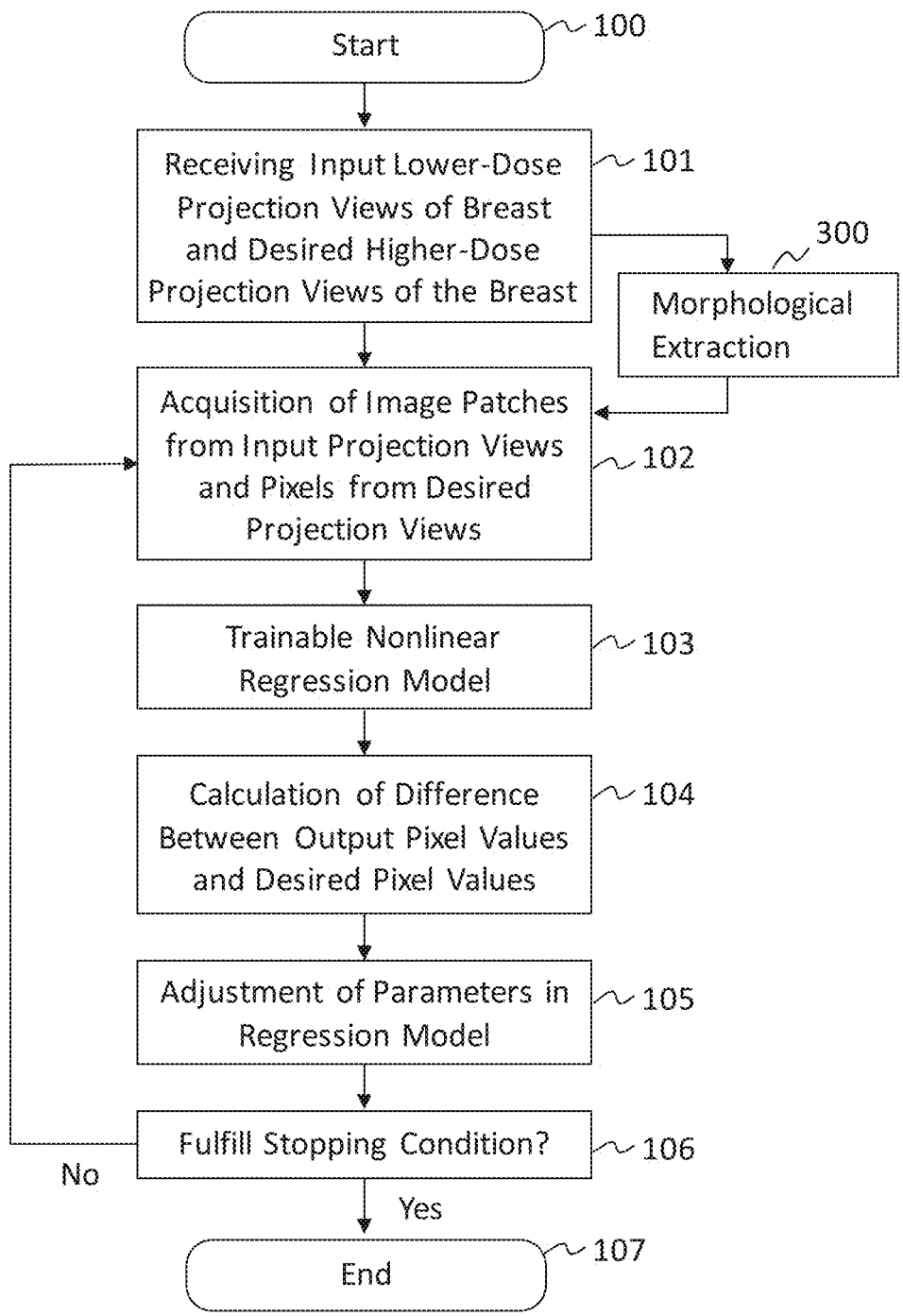
FIG. 2A shows a flow chart for a design step of a PTNR system for projection views or images.

FIG. 2A shows a flow chart for the design step of a PTNR system 118 and the process it carries out. First, in step 101, the PTNR system receives input lower-dose raw projection views (images) 114 of a breast with much inherent noise and the corresponding desired higher-dose raw projection views (images) 116 of a breast with less noise or artifact, which are ideal or desired images to the input lower-dose raw projection views (images). In other words, the input raw projection images 114 are of lower image quality, and the desired raw projection images 116 are of higher image quality. The desired raw projection images 116 may be acquired at the highest (or approximately the highest) radiation dose level that a tomosynthesis system can generate or can use for practical purposes. In step 102, image patches are acquired from the input raw projection images 114, and the corresponding pixels are acquired from the desired raw projection views images 116. Typically, a desired pixel corresponds to the center of an image patch. For example, when an image patch has 3×3 pixels, the corresponding location of the desired pixel is located at the second row and the second column in the image patch. In step 103, pixel values in the image patch form an N-dimensional input vector where N is the number of pixels in the image patch. The N-dimensional input vector is entered to the TNR model of PTNR system 118 as input. The TNR may be a regression model such as an artificial neural network regression model or some other practical regression model. Given the input vector, the TNR model with the current set of parameters outputs some output value. In step 104, a difference between the output pixel value and its desired pixel value obtained from the desired mammogram is calculated. The difference may be defined as a mean absolute error, a mean squared error, a Mahalanobis distance measure, and similarity measures such as mutual information. In step 105, parameters in the TNR are adjusted so as to minimize or at least reduce the difference. The adjustment may be made by using an optimization algorithm such as the steepest descent method or Newton's method. When an artificial neural network regression model is used as the regression model in the PTNR system 118, the error-back propagation algorithm [48] can be used to adjust the parameters in the model, i.e., weights between layers in the artificial neural network regression model. The error-back propagation algorithm is an example of the method for adjusting the parameters in the artificial neural network regression model. The formulation and derivation of the error-back propagation algorithm are described in [48] in detail. See, for example pages 161-175 in [48]. In step 106, when a predetermined stopping condition is met, the training is stopped; otherwise it goes back to step 102. The stopping condition may be set as, for example, (a) the average difference is smaller than a predetermined difference, or (b) the number of adjustments is greater than a predetermined number of adjustments.

Figure 2B:
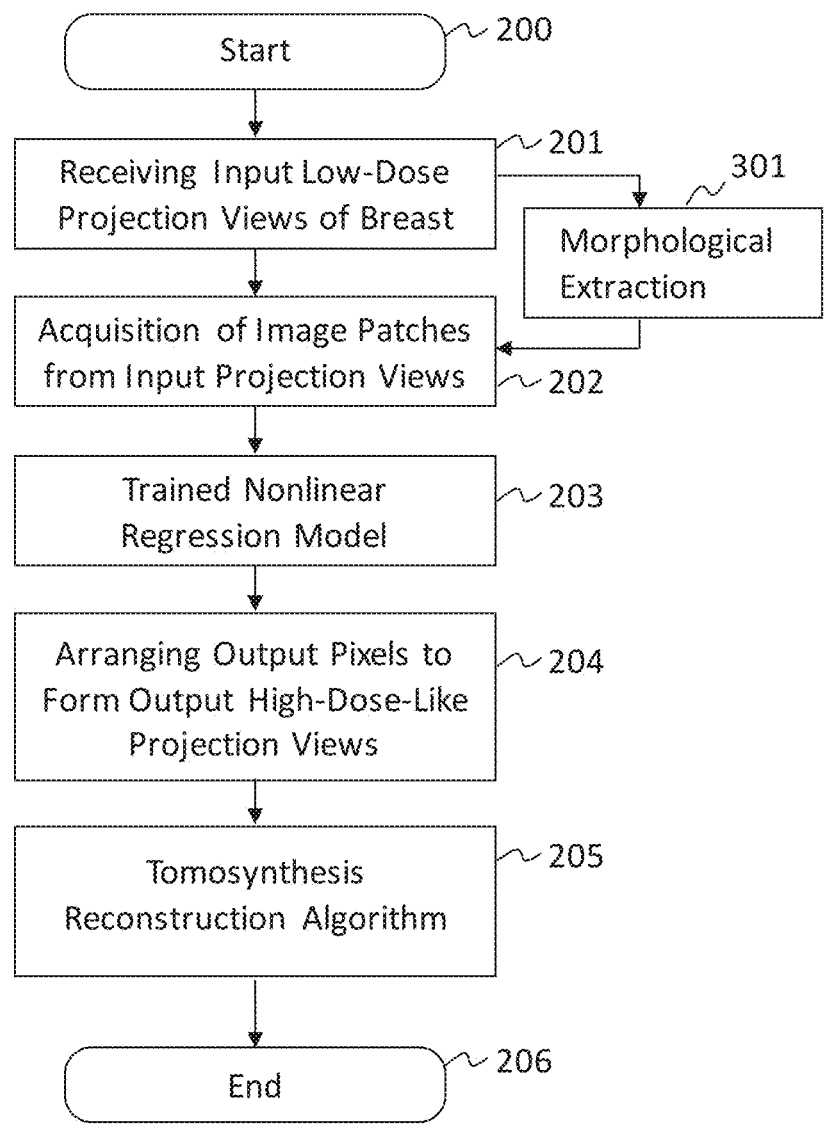
FIG. 2B shows a flow chart of a conversion step of a PTNR system for projection views or images.

FIG. 2B shows a flow chart of the conversion step of a PTNR system 118. This step is performed after the design step in FIG. 2A. First, in step 201, the designed PTNR system 118 receives input low-dose raw projection images 114*a* with noise inherent in images taken at a relatively low x-ray dose. In step 202, image patches are acquired from input low-dose raw projection images 114*a* that are different from the lower-dose raw projection images 114 used in the design step. Note that the low-dose raw projection images 114*a* do not have to be acquired at a lower radiation dose level than a standard dose, but they can be acquired at any radiation-dose level lower than the highest radiation dose that a tomosynthesis system can generate or use for practical purposes. In step 203, N dimensional input vectors comprising pixel values in the image patches are entered to the trained PTNR system 118 as input, and the trained PTNR system outputs output pixels. In step 204, the output pixels are arranged and put to the corresponding locations in the output images to form high-dose-like raw projection images 116*a* where noise and artifacts due to low radiation dose are reduced substantially. In step 205, from the "high-dose-like" projection images 116*a*, "high-dose-like" 3D tomosynthesis slices or slice images 120 are reconstructed by using a tomosynthesis reconstruction algorithm [40] such as filtered backprojection [41] and an iterative reconstruction method [42]. The "high-dose-like" 3D tomosynthesis slices 120 where noise and artifact are substantially reduced are expected to be similar to real high-dose 3D tomosynthesis slices; thus, they may be called "virtual" high-dose 3D tomosynthesis slices 120. Thus, the designed PTNR system 118 combined with the tomosynthesis reconstruction algorithm system 122 provide high-quality "virtual high-dose" 3D tomosynthesis slices or slice images 120.

In a modified PTNR system 118, a new step 300 is inserted between steps 101 and 102 in the design step of the PTNR process illustrated in FIG. 2A; and a new step 301 is inserted between steps 201 and 202 in the conversion step of the PTNR process illustrated in FIG. 2B. In step 300, morphologic elements including "impulsive" small high brightness regions in the input lower-dose 2D raw projection views (images) that are received in step 101 are enhanced by using mathematical morphologic filtering [49] and a median-filter-based method (described below in this paragraph). This step 300 aims to enhance or extract clinically important structures in 2D raw projection images such as breast tissue, masses (or tumors), architectural distortion (early sign of breast cancer), milk ducts, and breast cancer including ductal carcinoma in situ, and microcalcifications. Morphologic elements may represent such breast tissue patterns. The "impulsive" small high-brightness regions may represent microcalcifications. Since common breast tissue patterns appear like ridges and lines, line patterns may be enhanced by using a gray-scale mathematical morphologic filter with linear structural elements [49]. Ridge patterns may be enhanced by using a shape index operator [50, 51]. The "impulsive" small high brightness regions may be extracted by using the following median-filter-based method. Since a median filter can remove impulsive noise, subtraction of a median-filtered image from the original image gives enhancement (or extraction) of impulsive noise (small regions or outliers). Half-thresholding may be performed on the subtracted median-filtered image so that only bright (greater than a predetermined threshold value) "impulsive" noise (small regions) retains. By changing the kernel size of the median filter, "impulsive" high-brightness regions of a certain size can be enhanced (extracted). For example, a median filter with a kernel of 25 pixels can remove "impulsive" small regions smaller than or equal to 12 pixels.

In another implementation example of the PTNR system 118, multiple PTNR models are used in multiple regions in breast images, including breast images obtained with a mammography system, raw projection images obtained with a tomosynthesis system, and 3D reconstructed slices obtained with a tomosynthesis system. Each of multiple PTNR models is used to improve the performance for specific patterns. In the design step and conversion step, lower-dose and higher-mammographic images (including mammograms, raw projection views (images), and 3D tomosynthesis reconstructed slices) are divided into multiple segments. For example, a lower-dose or higher-dose image is divided into an outside breast region, a skin line region which is the boundary area between a breast and the outside of the breast, micro-calcification regions in the breast, a fatty breast region, a dense breast region, a mass region, and possibly other breast-tissue regions. Automated segmentation such as active-contour-model-based segmentation, active-shape-mode-based segmentation, level-set-based segmentation, region-growing-based segmentation, watershed segmentation, and machine-learning-based segmentation can be used before PTNR system 118, 400 or 402 (namely, between input images and the PTNR system) to segment such multiple areas in the lower-dose or higher-dose image in the design step and the conversion step in FIGS. 1A, 1B, 3A, and 3B. Manual segmentation can be used in the design step, as segmentation does not have to be automatic in that step. In the design step, each of multiple PTNR models is trained with training samples in a specific region. For example, one PTNR model is trained with training samples in micro-calcification regions, another PTNR model is trained with those in a skin line region, other PTNR model is trained with those in an outside breast region, and other PTNR model is trained with those in another breast-tissue region, and so on. After designing of multiple PTNR models in this way, each PTNR becomes a special purpose device or method for specific patterns in the specific region with which the PTNR is trained. For example, PTNR no. 1 is a special purpose device or method for micro-calcifications, PTNR no. 2 is a special purpose device or method for skin lines, PTNR no. 3 is a special purpose device or method for other breast tissue, and so on. In the conversion step, each of trained special purpose devices or methods in PTNR system 118 processes a specific region of the images that the PTNR is processing. Processed regions provided by PTNR system 118 are combined to form an entire high-dose-like output image 116a. In a mammography application, the output image forms a high-dose-like mammogram where noise and artifact are substantially reduced. The image quality of the high-dose-like mammogram obtained by multiple PTNR models is higher than that of such an image obtained by a single PTNR model. In the raw projection image application in tomosynthesis, the output images form high-dose-like raw projection images 116a. In the tomosynthesis reconstructed slice application, the output images form high-dose-like tomosynthesis reconstructed slices or slice images 403.

Applications of artificial neural network (ANN) techniques to medical pattern recognition and classification, called massive-training ANNs (MTANNs), are discussed in U.S. Pat. Nos. 6,819,790, 6,754,380, and 7,545,965, and U.S. Publication No. 2006/0018524. The MTANN techniques of U.S. Pat. Nos. 6,819,790 and 6,754,380, and U.S. Publication No. 2006/0018524 are developed, designed, and used for pattern recognition or classification, namely, to classify patterns into certain classes, e.g., classification of a region of interest in CT into an abnormal or normal. In other words, the final output of the MTANN is classes such as 0 or 1, whereas the final output of the methods and systems described in this patent specification, the PTNR, is continuous values (or images) or pixel values in breast images rather than images in which the pixels or voxels are characterized by Hounsfield numbers. The techniques of U.S. Pat. No. 7,545,965 are developed, designed, and used for enhancing or suppressing specific patterns such as ribs and clavicles in chest radiographs, whereas a PTNR system and method described in this patent specification is used for converting lower-dose raw projection views (images) 114a to higher-dose-like raw projection views (images) 116a. The patents and publications cited in this paragraph are hereby incorporated by reference.

In another implementation example of designing mode of operation of a PTNR system 118, simulated lower-dose raw projection views (images) 114d may be used instead of using real lower-dose raw projection views (images) 114. This implementation starts with higher-dose raw projection images 116 with less noise. Simulated breast image noise is added to the higher-dose raw projection images 116. Noise in raw projection images has two different types of noise components: quantum noise and electronic noise. Quantum noise in x-ray images can be modeled as signal-dependent noise, while electronic noise in x-ray images can be modeled as signal-independent noise. To obtain simulated lower-dose raw projection images 114b, simulated quantum and electronic noise is added to the higher-dose raw projection images 116 to convert them to images 114b.

In further examples, the PTNR system and method described above may be combined with other image-processing or pattern-recognition techniques, for example, a classifier such as a multi-layer perceptron, a support vector machine, linear discriminant analysis, or quadratic discriminant analysis.

The input lower-dose raw projection views (images) 114 or 114a and the desired higher-dose raw projection views (images) 116 or 116a preferably correspond to each other, namely, the location and orientation of the breast tissue are the same or very close in both images. This can be accomplished easily when a breast phantom is used. In some examples, the correspondence may be essentially exact, e.g., the lower-dose and higher-dose raw projection images taken at the same time or right after one another of the same patient or a breast phantom. In other examples, the lower-dose and higher-dose raw projection images may be taken at different magnifications or different times. In such cases, an image registration technique may be needed and used to match the locations of objects in the two raw projection images. The image registration may be rigid registration or non-rigid registration.

FIG. 3A shows a schematic diagram of the application of a 3D PTNR system or method to 3D tomosynthesis reconstructed slices or slice images in a design step. In the design step, the 3D PTNR system 400 for reconstructed slices is designed with input virtual high-dose 3D tomosynthesis reconstructed slices 120b with some noise and artifacts and the corresponding desired higher-dose 3D tomosynthesis reconstructed slices 401 with less noise or artifact. The input slices 120b can be obtained through the application of the trained PTNR system 118 for projection data combined with the tomosynthesis reconstruction algorithm system 122, or through the tomosynthesis reconstruction algorithm system 122 directly, without processing images 114b through system 118; in other words, they are like the virtual high-dose (or high-dose-like) reconstructed slices 120 as described above for FIGS. 1a and 1b or are slices that have been reconstructed from actual low-dose 2D tomosynthesis projection images 114b, respectively. The parameters in the 3D PTNR system 400 for reconstructed slices are adjusted to minimizing the difference between the output images of system 400 and the corresponding desired higher-dose 3D tomosynthesis reconstructed slices 401 derived from higher-dose raw projection views (images) 116b though processing with reconstruction system 122b. Through the designing process, the 3D PTNR system 400 for reconstructed slices learns to convert virtual high-dose (or high-dose-like) 3D reconstructed slices 120b with more noise and artifacts to higher-dose-like 3D tomosynthesis reconstructed slices being higher-image-quality with less noise or artifact. When virtual high-dose reconstructed slices 401 are used as input, the 3D PTNR system 400 improves further the image quality of the input virtual high-dose reconstructed slices, as the virtual high-dose reconstructed slices have still room for the improvement of the image quality.

FIG. 3B shows a schematic diagram of the application of a trained 3D PTNR system 402 to 3D tomosynthesis reconstructed slices in a conversion step. Once the 3D PTNR system 400 for reconstructed slices is trained, the resulting trained 3D PTNR system 402 does not require higher-dose 3D tomosynthesis reconstructed slices 401 anymore. When new high-dose-like reconstructed slices 120c obtained by the trained projection-image PTNR system 118c and reconstruction algorithm system 122c as illustrates in FIG. 3B are entered into the trained 3D PTNR system 402, the trained 3D PTNR system 402 for reconstructed slices would output images 403 similar to the desired images; in other words, it would output high-dose-like high-quality 3D tomosynthesis reconstructed slices or slice images 403 or "virtual high-dose" 3D tomosynthesis reconstructed slices 403 where noise and artifacts due to lower radiation dose are substantially reduced. Note that the new tomosynthesis images 114c do not have to be acquired at a lower radiation dose level than a standard dose (such as the one recommended by the current MQSA for screening mammograms or diagnostic mammograms), but they can be acquired at any radiation-dose level lower than the highest radiation dose that the tomosynthesis system can generate or can use for practical purposes. In addition to noise and artifact reduction, the conspicuity of breast tissue such as masses, architectural distortion, milk ducts, and breast cancer including ductal carcinoma in situ, and microcalcifications in the virtual high-dose 3D tomosynthesis reconstructed slices 403 is higher than that of such objects in lower-dose 3D tomosynthesis reconstructed slices. Therefore, the trained 3D PTNR system 402 for reconstructed slices is expected to improve the conspicuity of normal and abnormal structures in 3D tomosynthesis slices further.

3D mammograms discussed here may be tomosynthesis images taken on a digital tomosynthesis system.

Experiments

In order to design and evaluate an example of PTNR systems described above, ten tomosynthesis studies of two anthropomorphic breast phantoms with microcalcifications and lesions were acquired at five different radiation dose levels with a breast tomosynthesis system (Selenia Dimensions, Hologic, Bedford, Mass.). The radiation doses were changed by changing tube current-time product, while the tube voltage was fixed at 33 kVp. The tube current-time products, the corresponding tube currents, and the corresponding entrance dose in the acquisitions were as follows: 12, 24, 36, 52, and 99 mAs; 80, 165, 190, 190, and 190 and 133 mA; 1.35, 2.71, 4.04, 5.78 and 11.06 mGy, respectively. The tube current-time product of 52 mAs is considered the standard dose for the particular breast phantoms. Thus, the acquisitions were approximately 25, 50, 75, 100, and 200% of the standard dose. Other acquisition conditions were as follows: a spatial resolution (pixel size) of reconstructed slices was 0.117 mm/pixel; the matrix size of an image was 1,996×2,457 pixels; and the slice thickness was 0.9 mm.

Figure 4:
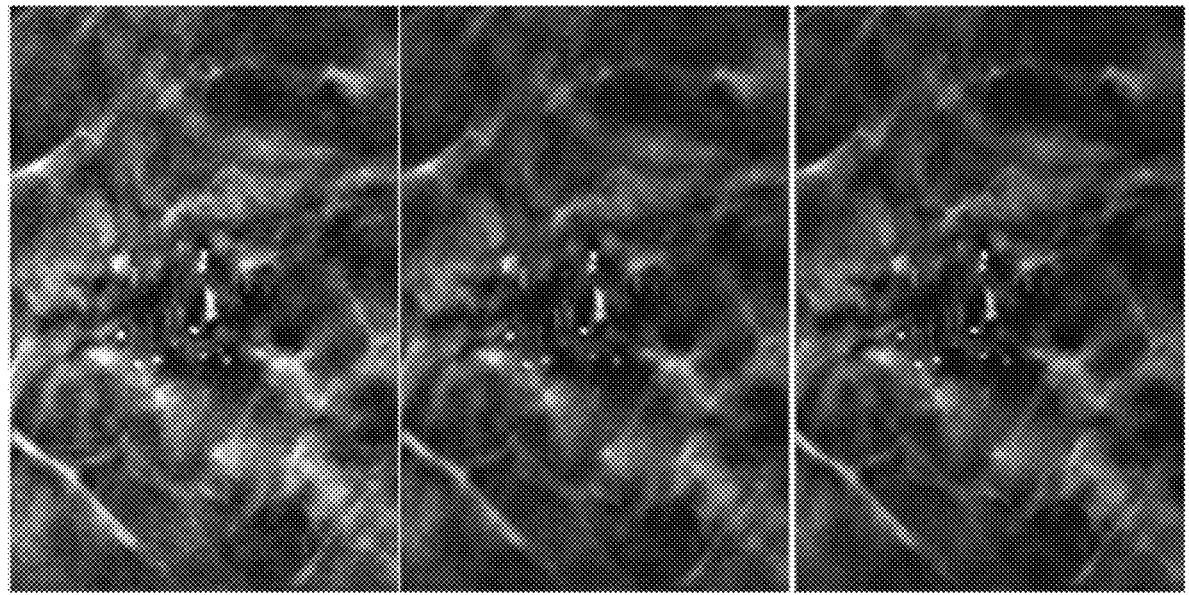
FIG. 4 shows comparisons of (a) the original low-dose (25% of the standard dose) reconstructed slice or slice image of a breast phantom, (b) the "virtual" high-dose (HD) reconstructed slice or slice image obtained by using the PTNR system, and (c) the corresponding "gold-standard" real HD (100% of the standard dose; full dose) reconstructed slice or slice image.

Two PTNR models were trained with an input lower-dose (12 mAs, 32 kVp, 1.35 mGy in entrance dose, 25% of the standard dose) raw projection images of each of the two breast phantoms and the corresponding higher-dose (99 mAs, 32 kVp, 200% of the standard dose) raw projection images. Each of the two trained PTNR models was applied to a non-training low-dose (12 mAs, 32 kVp, 1.35 mGy in entrance dose, 25% of the standard dose) raw projection images of the other breast phantom so that training and testing were completely separated. The trained PTNR models were able to convert the non-training low-dose raw projection images to "virtual high-dose" raw projection images using the systems and methods described above. Noise in the input low-dose raw projection images was reduced substantially in the "virtual" high-dose raw projection images by the PTNRs, while details of structures such as breast tissue, vascular structures, and micro-calcifications were maintained. Thus, through training, the PTNR system 118 learned the relationship between the input lower-dose raw projection images and desired higher-dose raw projection images. From the "high-dose-like" raw projection images, "high-dose-like" 3D tomosynthesis slices were reconstructed by using the tomosynthesis reconstruction algorithm system 122 as described above. FIG. 4 illustrates comparisons of the "virtual" high-dose (HD) reconstructed slice of the breast phantom obtained by using the PTNR system and method described above and the corresponding "gold-standard" real HD (100% of the standard dose; full dose) reconstructed slice. Noise in the original low-dose (25% of the standard dose) reconstructed slice of the breast phantom was reduced substantially in the "virtual" high-dose reconstructed slice by the PTNR system and method, while details of structures such as breast tissue, vascular structures, and micro-calcifications were maintained. The image quality of the "virtual" high-dose reconstructed slice was equivalent to that of the "gold-standard" full dose reconstructed slice.

Figure 5:
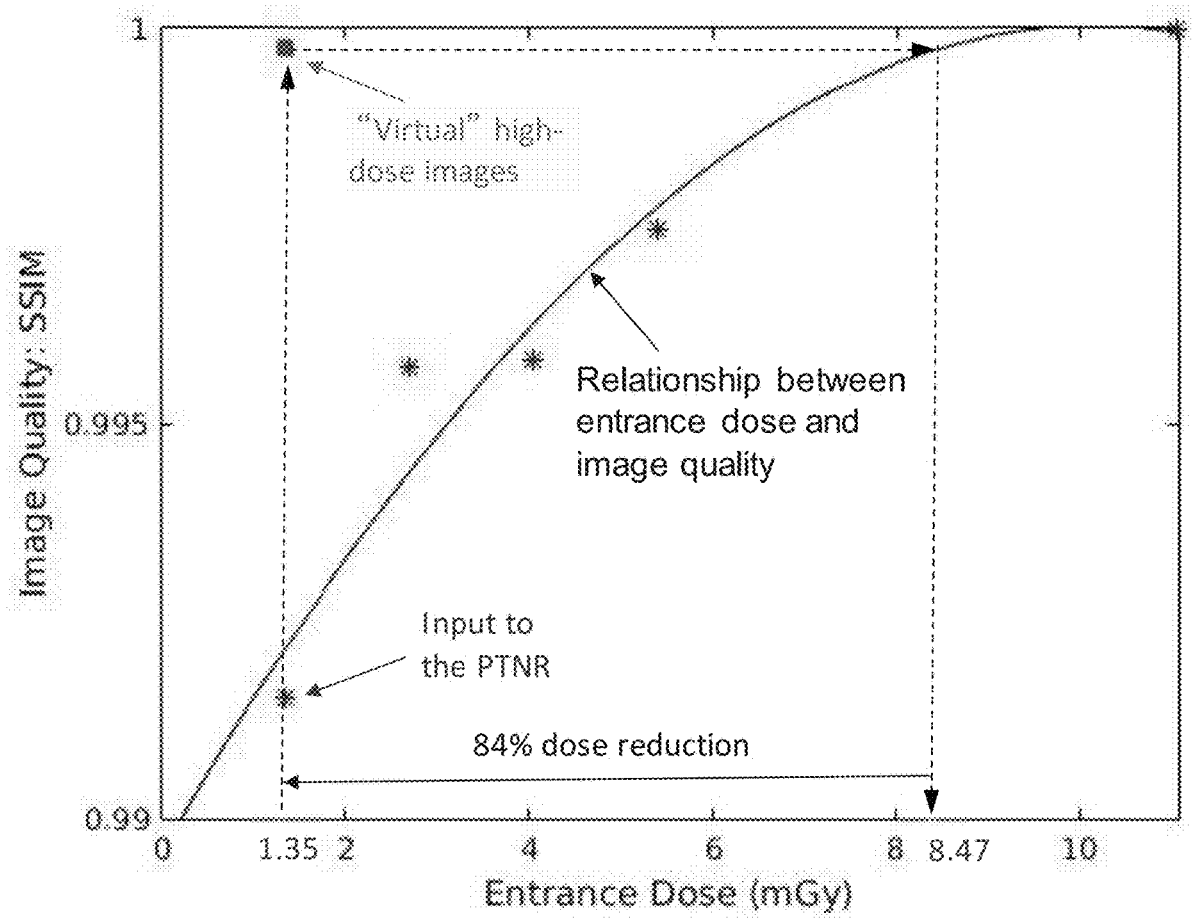
FIG. 5 shows the relationship between entrance radiation dose [mGy] and the image quality (in terms of the structural similarity (SSIM) index) in a breast phantom study.

To determine a dose reduction rate of the PTNR technology described in this patent specification, the dose reduction performance of the PTNR system 118 was measured. The structural similarity (SSIM) index [52] between the virtual HD images and the corresponding "gold-standard" real HD images was used for the evaluation, which is a widely accepted image quality measure that overcame the weakness of signal-to-noise ratio by taking spatial information into account. FIG. 5 shows the relationship between the image quality (SSIM) and the entrance dose. An average SSIM of the virtual HD images (obtained from 1.35 mGy low-dose images) of 0.9997 is equivalent to the image quality of 156% dose images (8.47 mGy), which corresponds to 84% (1−1.35/8.47) dose reduction.

Figure 6:
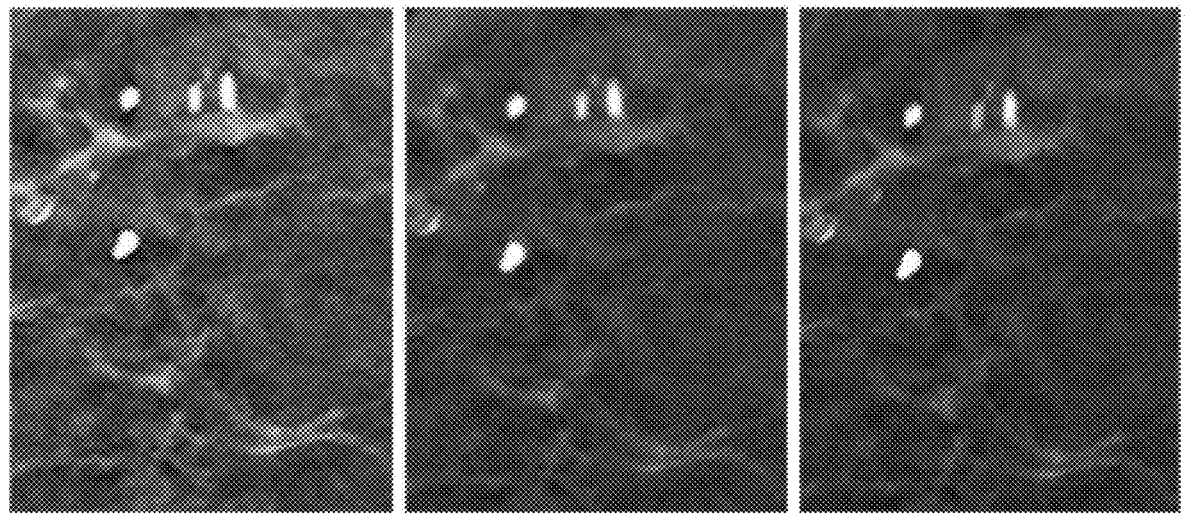
FIG. 6 shows comparisons of (a) an original low-dose (50% of the standard dose) reconstructed slice or slice image of a clinical patient case, (b) a "virtual" high-dose (HD) reconstructed slice of slice image obtained by using the PTNR system, and (c) the corresponding "gold-standard" real HD (100% of the standard dose; full dose) reconstructed slice or slice image.

To evaluate the performance and robustness of the PTNR technology, a PTNR system 118 trained with the anthropomorphic breast phantoms was applied to non-training 30 clinical cases. Each of the 30 patients had a low-dose (50% of the standard dose) tomosynthesis study in addition to the standard-dose (100%) tomosynthesis study with a breast tomosynthesis system (Selenia Dimensions, Hologic, Bedford, Mass.). The IRB protocol for this study has been approved, and the written patient consent was obtained from all 30 patients. The low dose tomosynthesis studies were obtained by changing tube current-time product, while the tube voltages were at 33±5 kVp. The tube current, tube current-time product, and entrance dose for standard-dose tomosynthesis studies ranged from 180±20 mA, 68±23 mAs, and 9.27±6.31 mGy, respectively, whereas those for low-dose tomosynthesis studies ranged from 163±38 mA, 32±14 mAs, and 4.55±3.30 mGy, respectively. Other acquisition conditions were as follows: a spatial resolution (pixel size) of reconstructed slices was 0.106±0.011 mm/pixel; the matrix size of an image was 1,996×2,457 or 1,890×2,457 pixels; and slice thickness was 0.88±0.05 mm The trained PTNR system 118 combined with the tomosynthesis reconstruction algorithm system 122 converted the non-training low-dose (50% of the standard dose) clinical tomosynthesis reconstructed slices to "virtual standard-dose" tomosynthesis reconstructed slices with less noise, as illustrated in FIG. 6. Noise in the input low-dose tomosynthesis reconstructed slice is reduced substantially in the "virtual" high-dose tomosynthesis reconstructed slice by the PTNR system, while details of structures such as breast tissue, vascular structures, and micro-calcifications are maintained, as demonstrated in FIG. 6(b). The virtual high-dose tomosynthesis reconstructed slices are similar to "gold-standard" real full-dose tomosynthesis reconstructed slice, as demonstrated in FIGS. 6(b) and (c). Thus, the image quality of the "virtual" high-dose reconstructed slice was equivalent to that of the "gold-standard" full dose reconstructed slice.

The processing time of the conversion process by the PTNR in the above example was 3.6 seconds for each breast on a PC (Intel i7-4790K CPU, 4 GHz). Since the algorithm of the PTNR is parallelizable, it can be shortened to 0.24 sec. on a computer with a Graphics Processing Unit (NVIDIA TITAN Z).

The PTNR technology described in this patent specification may be implemented in a medical imaging system such as a commercially available digital breast tomosynthesis system. The PTNR system 118 (and 124) may be implemented in a computer system or a viewing workstation. The PTNR process described above may be coded in software, firmware, and/or hardware. The PTNR process may be coded with any computer language such as C, C++, Basic, C #, Matlab, python, Fortran, Assembler, Java, and IDL. The PTNR process may be implemented in the Internet space, cloud-computing environment, or remote-computing environment. Converted images may be handled and stored in the Digital Imaging and Communications in Medicine (DICOM) format, and they may be stored in a picture archiving and communication system (PACS).

The PTNR technology can be implemented as a special-purpose computer or a general-purpose computer programmed to act as a special-purpose computer. When using a trained PTNR computer, a source provides lower image quality input tomosynthesis images, such as tomosynthesis images taken at radiation dose that is lower than a standard radiation dose for conventional tomosynthesis images. The source can be a conventional tomosynthesis unit, such as a digital breast tomosynthesis system that is set to take breast images at lower dose, or any other source of digital tomosynthesis that have been taken at lower-than-standard dose or otherwise have lower image quality that if they had been taken at a standard dose for conventional tomosynthesis studies. The PTNR computer is programmed and configured to apply the processes described above to convert input tomosynthesis images into output tomosynthesis images that have higher image quality, and supplies the output tomosynthesis images to a storage system such as hospital DICOM PACS facility and/or to a display unit such as conventional workstation commonly used in hospitals to view medical images provided from the DICOM PACS facility or directly from a medical imaging device or from some other source. When the system is used to train PTNR computer, source supplies lower image quality input tomosynthesis images that may have been taken at lower-than-standard radiation dose and/or may have resulted from deliberately degrading the image quality of standard-dose (or higher-dose) tomosynthesis images, and a source supplies matching desired tomosynthesis images. The desired tomosynthesis images may be actual tomosynthesis images taken at a radiation dose that is substantially higher than that used to take the input tomosynthesis images, for example at the dose recommended by MQSA for standard screening tomosynthesis images or a higher dose. Each input breast image is paired with a respective desired breast image. Using the processes described above, the PTNR computer is trained to produce an output breast image (including an example of a mammogram) from an input breast image (including a mammogram, for example), then compare the output breast image with the respective desired breast image, then adjust process parameters to reduce the difference between the output breast image and the desired breast image, and repeat these steps until the difference is less than a threshold or some other condition is met, such as exceeding a set number of iterations or reaching a selected threshold of the difference. The process parameters in the state at which iterations stop can become the parameters for a trained PTNR computer, and used thereafter to convert actual lower image quality input tomosynthesis images into higher image quality output tomosynthesis images. From time to time in the operation of a trained PTNR computer, a refreshing training process can be used. If a system is used solely with a trained PTNR computer, the parameters for the converting process can be pre-stored in computer, and can be updated or improved from time to time by replacement with a new set of parameters for the conversion processes.

The image conversion processes described above can be carried out through the use of a trainable/trained computer that is programmed with instruction downloaded from a computer program product that comprises computer-readable media such as one or more optical discs, magnetic discs, and flash drives storing, in non-transitory form, the necessary instructions to program computer to carry out the described processes involved in training the computer and/or using the trained computer to convert low image quality input tomosynthesis images into higher image quality tomosynthesis images. The instructions can be in a program written by a programmer of ordinary skill in programming based on the disclosure in this patent specification and the material incorporated by reference as well as general knowledge in programming technology.

While several embodiments are described, it should be understood that the technology described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements. There can be alternative ways of implementing both the processes and systems described herein that do not depart from the principles that this patent specification teaches. Accordingly, the present embodiments are to be considered as illustrative and not restrictive, and the body of work described herein is not to be limited to the details given herein, which may be modified within the scope and equivalents of the appended claims

What is claimed:

1. A x-ray breast imaging system comprising:
a low x-ray dose breast imaging structure configured to image a patient's breast with an x-ray beam to provide low-dose x-ray breast images each taken at an x-ray dose below a standard x-ray dose for an otherwise comparable x-ray image and having image quality below that of an otherwise comparable breast image taken at said standard x-ray dose;

a computer-implemented processor configured to apply computer processing to the low-dose x-ray images, said processing using training with breast images that have the image quality of comparable breast images taken at least at said standard x-ray dose, to thereby convert the low-dose x-ray images to respective higher-quality x-ray breast images comparable in image quality to otherwise comparable breast images taken at said standard x-ray dose;

wherein the processor is configured to process the low-dose images by processing each of respective multi-pixel patches of the low-dose images into a single pixel of the higher-quality images;

wherein said higher-quality x-ray breast images have reduced noise relative to said low-dose x-ray breast images and maintain details of breast structures; and a display configured to display said higher-quality x-ray images of the breast or breast images derived from said higher-quality breast images.

2. The x-ray breast imaging system of claim 1, in which the breast imaging structure is configured to take the low-dose x-ray images at doses corresponding to a dose that is between approximately 90% and 10% of a standard x-ray dose for otherwise comparable x-ray images.

3. The x-ray breast imaging system of claim 1, in which the low-dose x-ray images are two-dimensional tomosynthesis projection images taken at respective angles of an imaging x-ray beam with respect to the breast and the higher-quality breast images are higher-quality versions of said projection images, and in which the computer-implemented image processor further includes a computer-implemented image reconstruction system configured to process the higher-quality projection images into breast slice images comprising said breast images derived from said higher-quality breast images.

4. The x-ray breast imaging system of claim 1 in which the breast imaging structure is configured to take each of the low-dose x-ray images at an x-ray dose that is between 50% and 10% of the standard x-ray dose.

5. The x-ray breast imaging system of claim 1 in which the processor is configured to apply non-linear regression processing to the low-dose x-ray images and thereby convert them to the higher-quality images.

6. The x-ray breast imaging system of claim 1 in which the processor is further configured to extract morphologic elements corresponding to impulse areas of the low-dose images and use the extracted elements to improve converting the low-dose images into the higher-quality images.

7. A method of processing a mammogram, comprising:
obtaining input lower-quality breast images from an x-ray breast imaging system;
acquiring plural image patches from the input images;
entering the image patches into a computer-implemented, trainable regression model as input and obtaining from the model output pixel values corresponding to respective image patches;
wherein each of the input patches results in obtaining a corresponding a single output pixel value or pixel values of a corresponding output patch smaller than the input patch; and
arranging the output pixel values from the regression model into output breast images of higher image quality than the input images.

8. The method of claim 7, wherein the input images are tomosynthesis projection images taken at x-ray doses below a standard x-ray dose for otherwise comparable images.

9. The method of claim 7, wherein the input images are obtained from one or more of a breast tomosynthesis system, a mammography system, computer storage, a viewing workstation, a picture archiving and communication system, cloud computing, website, and the Internet.

10. The method of claim 9, wherein the tomosynthesis system or the mammography system is operating in a low-dose mode.

11. The method of claim 7, wherein the trainable regression model is a previously-trained regression model.

12. The method of claim 7, wherein the trainable regression model is at least one of an artificial neural network regression model, a support vector regression model, a nonlinear Gaussian process regression model, and a machine-learning regression model.

13. The method of claim 7, wherein the trainable regression model is a trainable regression model that was trained with lower image quality images and paired higher image quality images.

14. The method of claim 13, wherein the lower-quality images are lower-dose tomosynthesis projection images or mammograms, and the higher-quality images are higher-dose tomosynthesis projection images or mammograms.

15. The method of claim 7, further comprising:
extraction of morphologic elements that extracts morphologic elements from the input images; and
acquiring the plural image patches from both the input images and from the morphologic-elements-extracted images.

16. The method of claim 15, wherein the extraction of morphologic elements includes extraction of small high brightness regions.

17. The method of claim 15, wherein the plural image patches acquired from the input images are equal to or larger than the plural image patches acquired from the morphologic-elements-extracted image.

18. A method of processing x-ray breast images, comprising:
obtaining pairs of an input breast image and a desired breast image from a system;
acquiring plural multi-pixel image patches from the input images;
entering the image patches into a computer-implemented, trainable regression model as input to convert them into respective single output pixel values;
calculating a difference between the output pixel values from the trainable regression model and corresponding desired pixel values from the paired desired breast images; and
adjusting parameters in the trainable regression model based on the calculated difference to reduce noise in said input image but maintain details of breast structures including vascular structures and microcalcifications.

19. The method of claim 18, wherein the input image of a pair is a tomosynthesis projection image taken at an x-ray dose below a standard dose and the desired breast image is a projection tomosynthesis image taken at the standard dose or at a dose higher than the standard dose.

20. The method of claim 18, wherein the trainable regression model is one of an artificial neural network regression model, a support vector regression model, nonlinear Gaussian process regression model, and a machine-learning regression model.

21. The method of claim 18, wherein the calculated difference is a mean absolute error between output pixel values and corresponding desired pixel values, or a mean squared error between output pixel values and corresponding desired pixel values.

22. The method of claim 18, wherein the adjusting parameters in the trainable regression model comprise at least one of an error-back propagation algorithm, a steepest descent method, Newton's algorithm, and an optimization algorithm.

23. The method of claim 18, further comprising:
extraction of morphologic elements that extracts morphologic elements from the input images; and
wherein the plural image patches are acquired from both the input images and the morphologic-elements-extracted images.

24. The method of claim 23, wherein the extraction of morphologic elements includes extraction of small high brightness regions.

25. A system comprising:
a source of lower image quality input breast x-ray images;
a computer-implemented processor configured to acquire plural multi-pixel image patches from the input images;
said processor being further configured to apply a trained regression model processing to the acquired image patches and provide single output pixel values each corresponding to a respective image patch;
said processor being further configured to arrange the output pixel values from the regression model into output breast images of higher image quality than the respective input images; and
a display associated with the processor to receive and display the output images.

26. The system of claim 25, in which said processor is configured to acquire respective patches from plural regions in which the input images are segmented, and is further configured to apply differently trained regression models to the patches from the respective regions.

27. A system comprising:
a source configured to provide a pair of an input breast x-ray image and a desired breast image;
a computer-implemented trainable regression model facility configured to acquire plural multi-pixel image patches from the input image and apply regression model processing thereto to produce single output pixels that are produced from respective patches of the input image and form an output image, calculate a difference between the desired image and the output image and change parameters of the regression model to reduce the difference, and repeat the steps of applying the regression model, calculating the difference and changing parameters until a threshold condition is met, and outputting a final output breast image upon meeting the threshold condition; and
a display facility selectively displaying the output breast image.

28. The system of claim 27, in which said model facility is configured to acquire respective patches from plural regions in which the input image and the desired image are segmented, and to apply respective regression model processing to the patches from the respective regions.

* * * * *